United States Patent [19]

Mikkelsen

[11] Patent Number: Plant 5,961

[45] Date of Patent: Apr. 28, 1987

[54] KALANCHOE PLANT NAMED TROPICANA

[75] Inventor: James C. Mikkelsen, Ashtabula, Ohio

[73] Assignee: Mikkelsens, Inc., Ohio

[21] Appl. No.: 782,459

[22] Filed: Oct. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Tropicana, characterized by its orange-red flower; floriferous habit; superior self-branching; time to flowering of eleven weeks in summer to thirteen weeks in winter; requirement for growth regulation to control peduncle and pedicel elongation; relatively large, dark green foliage which maintains color after several months of flowering; excellent flower keeping qualities, and by its resistance to disease.

1 Drawing Figure

1

The present invention relates to a new and distinct cultivar of Kalanchoe plant, botanically known as *Kalanchoe blossfeldiana,* and known by the cultivar name Tropicana. Tropicana was developed by me through controlled breeding by crossing Mikkelsen seedling No. 79-2328-37 (seed parent) with Regulus, disclosed in U.S. Plant Pat. No. 4,817 (pollen parent).

Asexual reproduction by stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Tropicana is characterized by its high degree of self branching and floriferous flowering habit.
2. Branching is better than the cultivar Bali (U.S. Plant Pat. No. 5,348), Regulus or Mercur (U.S. Plant Pat. No. 5,347).
3. Tropicana is similar in color to Bali, lighter than Mercur and deeper than Regulus, and is more floriferous than all.
4. Bali is slightly taller than Tropicana, and Mercur and Regulus are slightly more dwarf.
5. Flowering time is 11 weeks in summer and 13 weeks in winter, which is approximately 5 days later than Bali, Regulus and Mercur calculated from the start of short days, as tested in Ashtabula, Ohio.
6. After flower initiation, plants must be treated with B-9 in all seasons to reduce peduncle and pedicel elongation.
7. Flower size is larger than Mercur and Regulus and similar to Bali.
8. Leaf size is larger than Regulus and Mercur and equal to Bali, with leaf color being darker green than Bali and Regulus but similar in color to Mercur.
9. Leaf tip is not as acute as Bali, but more obtuse like Mercur and Regulus.
10. Leaf margins of Tropicana are crenate like Mercur but not as rounded; not as finely crenate as Regulus and not as dentate as Bali.

The accompanying colored photograph illustrates in perspective view the overall appearance of Tropicana, showing the colors as true as it is reasonably possible to obtain in a colored reproduction of this type.

2

The following is a detailed description of my new Kalanchoe cultivar based on plants produced under commercial practices in the greenhouses of Mikkelsens, Inc., Ashtabula, Ohio. Color references are made to The Royal Horticultural Society Colour Chart (R.H.S.) except where general terms of ordinary dictionary significance are used.

Parentage: A controlled cross between Mikkelsen seedling No. 79-2328-37 and Regulus.

Propagation:

(A) *Type cutting.*—Short stem cuttings up to 2 cm long.

(B) *Time to root.*—10 days at 21° C. summer, 14 days at 21° C. winter.

(C) Rooting habit.—Many fine fibrous roots.

Plant description:

(A) *Form.*—Short, compact, upright; best suited for growing and scheduling practices in a 10 cm pot.

(B) *Habit of growth.*—Moderate rate of growth with branching from nearly every node; basal branching is pronounced.

(C) *Foliage.*—Leaves simple, opposite. (1) Size: Average full grown leaf of flowering plant in a 10 cm pot is approximately 90 mm long and 60 mm wide. (2) Shape: Obovate, obtuse apex and rounded base. (3) Texture: Glabrous, coriaceous, succulent. (4) Margin: Crenate. (5) Color: Young foliage, top side 137B; under side 137C. Mature foliage top side 147A, underside 147B.

Flowering description:

(A) *Flowering habits.*—Cyme inflorescence; each shoot is formed by dichotomous branching starting with the opening of the terminal flower of the main axis, followed by terminal flower of the side branching, continuing with subsequent development of branches in the inflorescence. Major inflorescence is 80 to 85 mm in diameter, and lateral inflorescences are 50 to 60 mm in diameter in a 10 cm pot. Extremely good flower keeping qualities.

(B) *Natural flowering season.*—Mid-January. Flowering time under controlled daylength at 20° C. in summer is 11 weeks; in winter, 13 weeks.

Flowering time depends on temperature, light intensity, and other growing conditions.

(C) *Flower buds.*—Oblong up to 9 mm long, developing to tubular as flower petals mature, sheathed with four light green sepals; corolla at maturity is 11 mm long.

(D) *Flowers borne.*—Compound dichasial cymes; peduncle 5 mm in diameter, with peduncle length depending on growing conditions and B-9 application; pedicels up to 9 mm long.

(E) *Quantity of flowers.*—Highly floriferous. The main axis has over 125 flowers, and lateral branches have more than 75 flowers, with 6 to 8 lateral branches in a 10 cm pot; flowers are longer lasting than comparison cultivars.

(F) *Petals.*—(1) Shape: Nearly rounded, top cuspidate. (2) Color: Top side when opening, 33A, fading to 33B; under side 37A at tip, 32D at center. (3) Number of petals: Four (4) united in corolla; petals are 6 mm in diameter; flowers are approximately 14 mm in diameter.

(G) *Reproductive organs.*—(1) Stamens: Eight (8) in number. (a) Anthers: Flat, elliptical, yellow in color. (b) Filament color: Light green. (c) Pollen color: Yellow. (2) Pistels (a) Stigma: Flat, greenish white when immature to white when mature. (b) Style color: Light green. (c) Ovaries: Four (4) in number, celled, size 7 mm, light green color.

Disease resistance: Very resistant to mildew. No other disease problems seen to date, including foliar diseases which some cultivars are susceptible to as plants age.

I claim:

1. A new and distinct cultivar of Kalanchoe plant named Tropicana, as illustrated and described, and particularly characterized by its orange-red flowers; floriferous habit; superior self-branching; time to flowering of eleven weeks in summer to thirteen weeks in winter; requirement for growth regulation to control peduncle and pedicel elongation; relatively large, dark green foliage which maintains color after several months of flowering; excellent flower keeping qualities, and by its resistance to disease.

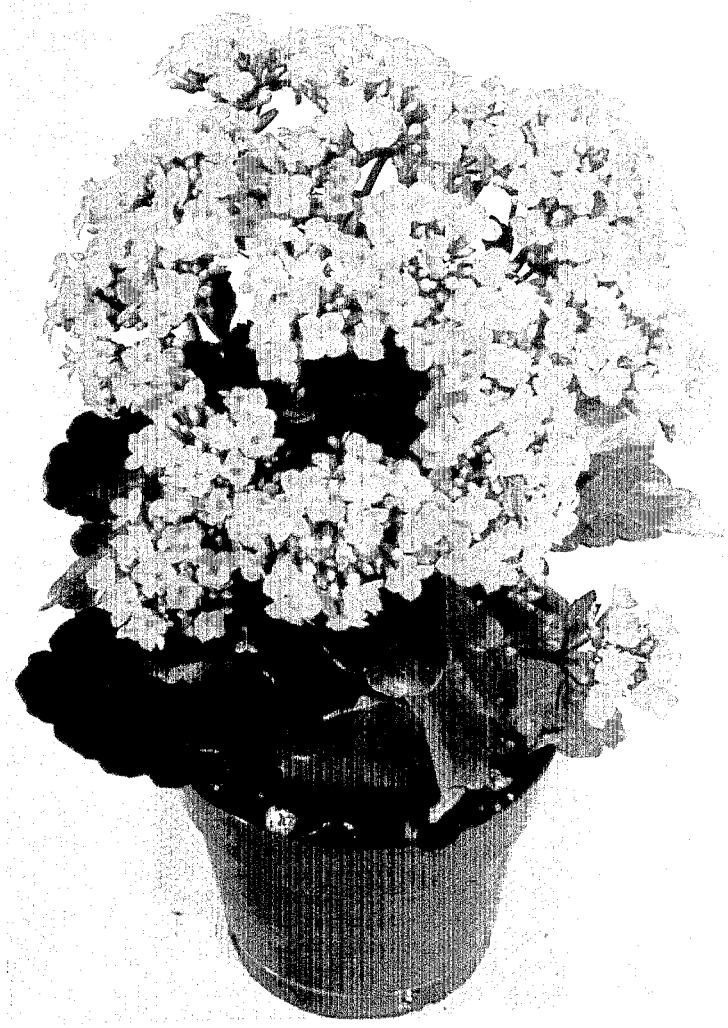

* * * * *